US010174342B2

(12) United States Patent
Hofrichter et al.

(10) Patent No.: US 10,174,342 B2
(45) Date of Patent: Jan. 8, 2019

(54) ENZYMATIC HYDROXYLATION OF ALIPHATIC HYDROCARBON

(71) Applicant: Novozymes A/S, Bagsvaerd (DK)

(72) Inventors: Martin Hofrichter, Dresden (DE); Katrin Scheibner, Jena (DE); Rene Ullrich, Zittau (DE); Matthias Kinne, Gorlitz (DE); Sebastian Peter, Zittau (DE); Henrik Lund, Vaerloese (DK); Lisbeth Kalum, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/887,636

(22) Filed: Feb. 2, 2018

(65) Prior Publication Data
US 2018/0171365 A1 Jun. 21, 2018

Related U.S. Application Data

(62) Division of application No. 15/349,024, filed on Nov. 11, 2016, now Pat. No. 9,909,147, which is a division of application No. 14/842,953, filed on Sep. 2, 2015, now Pat. No. 9,534,238, which is a division of application No. 13/637,716, filed as application No. PCT/EP2011/054761 on Mar. 28, 2011, now Pat. No. 9,222,109.

(60) Provisional application No. 61/318,582, filed on Mar. 29, 2010.

(30) Foreign Application Priority Data

Mar. 28, 2010 (EP) ..................................... 10158092
Mar. 28, 2010 (EP) ..................................... 10158093

(51) Int. Cl.
| | | |
|---|---|---|
| C12P 7/02 | (2006.01) |
| C12P 7/04 | (2006.01) |
| C12N 9/02 | (2006.01) |
| C12N 9/08 | (2006.01) |
| C12P 7/42 | (2006.01) |
| C12P 7/00 | (2006.01) |

(52) U.S. Cl.
CPC .................. *C12P 7/04* (2013.01); *C12P 7/02* (2013.01); *C12P 7/42* (2013.01); *C12Y 111/02001* (2013.01); *C12N 9/0071* (2013.01); *C12P 7/00* (2013.01); *C12Y 114/14001* (2013.01)

(58) Field of Classification Search
CPC . C12P 7/04; C12P 7/02; C12N 9/0065; C12N 9/007; C12Y 14/14001

USPC .................................. 435/132, 155, 189, 192
See application file for complete search history.

(56) References Cited

U.S. PATENT DOCUMENTS

| 7,524,664 B2 | 4/2009 | Arnold et al. |
| 2005/0059128 A1 | 3/2005 | Arnold |
| 2010/0279366 A1 | 11/2010 | Pecyna et al. |

FOREIGN PATENT DOCUMENTS

| DE | 10332065 A | 1/2005 |
| WO | 2006/034702 A1 | 4/2006 |
| WO | 2008/028526 A1 | 3/2008 |
| WO | 2008/119780 A2 | 10/2008 |
| WO | 2013021060 A1 | 2/2013 |
| WO | 2013021061 A1 | 2/2013 |
| WO | 2013021062 A2 | 2/2013 |
| WO | 2013079531 A2 | 6/2013 |
| WO | 2013079533 A1 | 6/2013 |

OTHER PUBLICATIONS

Bell et al., Journal of Royal Society of Chemistry, Dalton Trans., pp. 21-23 (2003).
Cirino et al., Advanced Synthesis and Catalysis, vol. 344, No. 9, pp. 932-937 (2002).
Devos et al., Proteins: Structure, Function and Genetics, vol. 41, pp. 98-107 (2000).
Hofrichter et al., Applied Microbiology and Biotechnology, vol. 87, No. 3, pp. 871-897 (2010).
Kinne et al., Journal of Biological Chemistry, vol. 284, No. 43, pp. 29343-29349 (2009).
Kisselev et al., Structure, vol. 10, pp. 8-9 (2002).
Kluge et al., Applied Microbiology and Biotechnology, vol. 75, pp. 1473-1478 (2007).
Ullrich et al., Applied and Environmental Microbiology, vol. 70, No. 8, pp. 4575-4581 (2004).
Ullrich et al., FEBS Letters, vol. 579, pp. 6247-6250 (2005).
Whisstock et al., Quarterly Reviews of Biophysics, vol. 36, No. 3, pp. 307-340 (2003).
Witkowski et al., Biochemistry, vol. 38, pp. 11643-11650 (1999).
Babot et al, 2013, Biotechnol Bioeng 110(9), 2323-2332.
Gutierrez et al, 2011, Arch Biochem Biophys 514, 33-43.
Peter et al, 2011, FEBS Journal 278, 3667-3675.

*Primary Examiner* — Robert B Mondesi
*Assistant Examiner* — Mohammad Y Meah
(74) *Attorney, Agent, or Firm* — Eric J. Fechter

(57) ABSTRACT

The invention relates to enzymatic methods for hydroxylation in position 2 or 3 of substituted or unsubstituted, linear or branched aliphatic hydrocarbons.

19 Claims, No Drawings
Specification includes a Sequence Listing.

ENZYMATIC HYDROXYLATION OF ALIPHATIC HYDROCARBON

CROSS-REFERENCE TO RELATED APPLICATIONS

This application is a divisional of U.S. application Ser. No. 15/349,024 filed on Nov. 11, 2016, now U.S. Pat. No. 9,909,147, which is a divisional of U.S. application Ser. No. 14/842,953 filed on Sep. 2, 2015, now U.S. Pat. No. 9,534,238 which is a divisional of U.S. application Ser. No. 13/637,716 filed on Sep. 27, 2012, now U.S. Pat. No. 9,222,109, which is a 35 U.S.C. 371 national application of PCT/EP2011/054761 filed Mar. 28, 2011, which claims priority or the benefit under 35 U.S.C. 119 of European application nos. 10158092.6 and 10158093.4 filed on Mar. 28, 2010 and Mar. 28, 2010 and U.S. provisional application No. 61/318,582 filed on Mar. 29, 2010. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to the use of polypeptides having peroxygenase activity for site specific hydroxylation of aliphatic hydrocarbons.

Background

A peroxygenase denoted AaP from the agaric basidiomycete strain *Agrocybe aegerita* (strain TM-A1) was found to oxidize aryl alcohols and aldehydes. The AaP peroxygenase was purified from *A. aegerita* TM A1 by several steps of ion chromatography and SDS-PAGE, the molecular weight was determined and the N-terminal 14 amino acid sequence was determined after 2-D electrophoresis but the encoding gene was not isolated (Ullrich et al., 2004, *Appl. Env. Microbiol.* 70(8): 4575-4581).

WO 2006/034702 discloses methods for the enzymatic hydroxylation of non-activated hydrocarbons, such as, naphtalene, toluol and cyclohexane, using the AaP peroxygenase enzyme of *Agrocybe aegerita* TM A1. This is also described in Ullrich and Hofrichter, 2005, *FEBS Letters* 579: 6247-6250.

WO 2008/119780 discloses eight different peroxygenases from *Agrocybe aegerita, Coprinopsis cinerea, Laccaria bicolor* and *Coprinus radians*; also shown as SEQ ID NOs: 1-8 in the present application.

DE 103 32 065 A1 discloses methods for the enzymatic preparation of acids from alcohols through the intermediary formation of aldehydes by using the AaP peroxygenase enzyme of *Agrocybe aegerita* TM A1.

A method was reported for the rapid and selective spectrophotometric direct detection of aromatic hydroxylation by the AaP peroxygenase (Kluge et al., 2007, *Appl. Microbiol. Biotechnol.* 75: 1473-1478).

It is well-known that a direct regioselective introduction of oxygen functions (oxygenation) into organic molecules constitutes a problem in chemical synthesis. It is particularly difficult to catalyse the selective hydroxylation of aliphatic carbohydrates. The products may be used as important intermediates in a wide variety of different syntheses.

In particular the chemical hydroxylation of alkanes is relatively complex, requires aggressive/toxic chemicals/catalysts and leads to a series of undesired by-products.

It is known that an intracellular enzyme, methane monooxygenase (MMO, EC 14.13.25), oxygenates/hydroxylates the terminal carbon of some hydrocarbons. The MMO enzyme consists of several protein components and is formed by methylotrophic bacteria (e.g. *Methylococcus capsulatus*); it requires complex electron donors such as NADH or NADPH, auxiliary proteins (flavin reductases, regulator protein) and molecular oxygen ($O_2$). The natural substrate of MMO is methane, which is oxidized to methanol. As a particularly unspecific biocatalyst, MMO oxygenates/hydroxylates, as well as methane, a series of further substrates such as n-alkanes and their derivatives, cycloalkanes, aromatics, carbon monoxide and heterocycles. Utilization of the enzyme in biotechnology is currently not possible, since it is difficult to isolate, like most intracellular enzymes, it is of low stability, and the cosubstrates required are relatively expensive.

SUMMARY OF THE INVENTION

In a first aspect, the inventors of the present invention have provided a method for hydroxylation in position 2 or 3 of either end of a substituted or unsubstituted, linear or branched, aliphatic hydrocarbon having at least 3 carbons and having a hydrogen attached to the carbon in position 2 or 3, comprising contacting the aliphatic hydrocarbon with hydrogen peroxide and a polypeptide having peroxygenase activity; wherein the polypeptide comprises:

a) an amino acid sequence which has at least 50% identity to SEQ ID NO:1, SEQ ID NO:2, SEQ ID NO:3, SEQ ID NO:4, SEQ ID NO:5, SEQ ID NO:6, SEQ ID NO:7, or SEQ ID NO:8; and b) an amino acid sequence represented by one or more of the following motifs:

```
                                    (SEQ ID NO: 9)
Motif I:     [FL]XX[YF]S[AN]X[FHY]G[GN]GX[YF]N;

(SEQ ID NO: 10)
Motif II:    G[GN]GX[YF]NXX[VA]AX[EH][LF]R;

(SEQ ID NO: 11)
Motif III:   RXXRI[QE][DEQ]S[IM]ATN;

(SEQ ID NO: 12)
Motif IV:    S[IM]ATN[PG][EQN][FM][SDN][FL];

(SEQ ID NO: 13)
Motif V:     P[PDK][DG]F[HFW]R[AP];

(SEQ ID NO: 14)
Motif VI:    [TI]XXXLYPNP[TK][GV].
```

In an embodiment, the aliphatic hydrocarbon is a fatty acid.

In another aspect is provided a method for hydroxylation in position 2 or 3 of the terminal end of an acyl group of a lipid, comprising contacting the lipid with hydrogen peroxide and a polypeptide having peroxygenase activity; wherein the polypeptide comprises:

a) an amino acid sequence which has at least 50% identity to SEQ ID NO:1, SEQ ID NO:2, SEQ ID NO:3, SEQ ID NO:4, SEQ ID NO:5, SEQ ID NO:6, SEQ ID NO:7, or SEQ ID NO:8; and b) an amino acid sequence represented by one or more of the following motifs:

Motif I:     [FL]XX[YF]S[AN]X[FHY]G[GN]GX[YF]N   (SEQ ID NO: 9)

Motif II:    G[GN]GX[YF]NXX[VA]AX[EH][LF]R   (SEQ ID NO: 10)

Motif III:   RXXRI[QE][DEQ]S[IM]ATN   (SEQ ID NO: 11)

Motif IV:   S[IM]ATN[PG][EQN][FM][SDN][FL]   (SEQ ID NO: 12)

Motif V:     P[PDK][DG]F[HFW]R[AP]   (SEQ ID NO: 13)

Motif VI:    [TI]XXXLYPNP[TK][GV].   (SEQ ID NO: 14)

In further aspects, the invention provides uses of polypeptides having peroxygenase activity for removal of lipid containing stains from laundry; and for reducing unpleasant odor from laundry.

Definitions

Peroxygenase activity: The term "peroxygenase activity" is defined herein as the capability to hydroxylate naphtalene using hydrogen peroxide, also referred to as "unspecific peroxygenase", EC 1.11.2.1. This is a heme-thiolate protein. Enzymes of this type include glycoproteins secreted by agaric basidiomycetes. They catalyse the insertion of an oxygen atom from $H_2O_2$ into a wide variety of substrates, including aromatic rings such as naphthalene, toluene, phenanthrene, pyrene and p-nitrophenol, recalcitrant heterocycles such as pyridine, dibenzofuran, various ethers (resulting in O-dealkylation) and alkanes such as propane, hexane and cyclohexane. Additional reactions which may be catalysed by peroxygenases include hydroxylation, epoxidation, N-oxidation, sulfooxidation, O- and N-dealkylation, bromination and one-electron oxidations. They have little or no activity toward chloride.

For purposes of the present invention, peroxygenase activity is determined according to the spectrophotometric procedure described by Kluge et al. (2007, *Appl. Microbiol. Biotechnol.* 75: 1473-1478).

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the peroxygenase activity of the mature polypeptide of SEQ ID NO: 1, 2, 3, 4, 5, 6, 7 or 8.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having peroxygenase activity that is in its final form following translation and any post-translational modifications, such as N-terminal processing, C-terminal truncation, glycosylation, phosphorylation, etc. In a preferred aspect, the mature polypeptide has the amino acid sequence shown in positions 1 to 330 of SEQ ID NO:1 based on the N-terminal peptide sequencing data (Ullrich et al., 2004, *Appl. Env. Microbiol.* 70(8): 4575-4581), elucidating the start of the mature protein of AaP peroxygenase enzyme. In another preferred aspect, the mature polypeptide has the amino acid sequence shown in positions 1 to 328 of SEQ ID NO:2.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment–
Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; emboss.org), preferably version 3.0.0 or later. The optional parameters used are gap open penalty of 10, gap extension penalty of 0.5, and the EDNA-FULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment–Total Number of Gaps in Alignment).

Modification: The term "modification" means herein any chemical modification of the polypeptide consisting of the mature polypeptide of SEQ ID NO: 1, 2, 3, 4, 5, 6, 7 or 8; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

DETAILED DESCRIPTION OF THE INVENTION

Polypeptides Having Peroxygenase Activity (Peroxygenases)

The present invention relates to uses of an isolated polypeptide, which is preferably recombinantly produced, having peroxygenase activity, which comprises an amino acid sequence having at least 50% identity, preferably at least 55%, 60%, 65%, 70%, 75%, 80%, 85%, 90%, 95%, 97%, or 98% identity to the polypeptide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

In a preferred embodiment, the polypeptide comprises an amino acid sequence represented by one or more of the following motifs, preferably comprising two or more, three or more, four or more, five or six of the following motifs.

```
                                          (SEQ ID NO: 9)
Motif I:      [FL]XX[YF]S[AN]X[FHY]G[GN]GX[YF]N;

(SEQ ID NO: 10)
Motif II:     G[GN]GX[YF]NXX[VA]AX[EH][LF]R;

(SEQ ID NO: 11)
Motif III:    RXXRI[QE][DEQ]S[IM]ATN;

(SEQ ID NO: 12)
Motif IV:     S[IM]ATN[PG][EQN][FM][SDN][FL];

(SEQ ID NO: 13)
Motif V:      P[PDK][DG]F[HFW]R[AP];

(SEQ ID NO: 14)
Motif VI:     [TI]XXXLYPNP[TK][GV].
```

In another embodiment, the polypeptide comprises an amino acid sequence having a substitution, deletion, and/or insertion of one or several amino acids of the mature polypeptide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

In yet another embodiment, the polypeptide of the first aspect comprises or consists of the amino acid sequence of SEQ ID NO:1, SEQ ID NO:2, SEQ ID NO:3, SEQ ID NO:4, SEQ ID NO:5, SEQ ID NO:6, SEQ ID NO:7, or SEQ ID NO:8; or a fragment thereof having peroxygenase activity; preferably the polypeptide comprises or consists of the mature polypeptide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., peroxygenase activity) to identify amino acid residues critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and regiondirected mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 is 10, preferably 9, more preferably 8, more preferably 7, more preferably at most 6, more preferably 5, more preferably 4, even more preferably 3, most preferably 2, and even most preferably 1.

It is preferable that the polypeptide of the first aspect is encoded by the polynucleotide contained in the plasmid which is contained in *E. coli* NN049991 deposited 14 Mar. 2008 under the terms of the Budapest Treaty with the DSMZ under accession number DSM 21289; or which is encoded by the polynucleotide contained in the plasmid which is contained in *E. coli* NN049992 deposited 14 Mar. 2008 under the terms of the Budapest Treaty with the DSMZ under accession number DSM 21290.

Another preferred embodiment relates to the polypeptide of the first aspect of the invention, wherein the mature polypeptide is amino acids 1 to 330 of SEQ ID NO:1.

Yet another preferred embodiment relates to the polypeptide of the first aspect of the invention, wherein the mature polypeptide is amino acids 1 to 328 of SEQ ID NO:2.

Yet another preferred embodiment relates to the polypeptide of the first aspect of the invention, wherein the mature polypeptide is amino acids 1 to 344 of SEQ ID NO:4.

Hydrogen Peroxide

The hydrogen peroxide required by the peroxygenase may be provided as an aqueous solution of hydrogen peroxide or a hydrogen peroxide precursor for in situ production of hydrogen peroxide. Any solid entity which liberates upon dissolution a peroxide which is useable by peroxygenase can serve as a source of hydrogen peroxide. Compounds which yield hydrogen peroxide upon dissolution in water or an appropriate aqueous based medium include but are not limited to, metal peroxides, percarbonates, persulphates, perphosphates, peroxyacids, alkyperoxides, acylperoxides, peroxyesters, urea peroxide, perborates and peroxycarboxylic acids or salts thereof.

Another source of hydrogen peroxide is a hydrogen peroxide generating enzyme system, such as an oxidase together with a substrate for the oxidase. Examples of combinations of oxidase and substrate comprise, but are not limited to, amino acid oxidase (see e.g. U.S. Pat. No. 6,248,575) and a suitable amino acid, glucose oxidase (see e.g. WO 95/29996) and glucose, lactate oxidase and lactate, galactose oxidase (see e.g. WO 00/50606) and galactose, and aldose oxidase (see e.g. WO 99/31990) and a suitable aldose.

By studying EC 1.1.3._, EC 1.2.3._, EC 1.4.3._, and EC 1.5.3._ or similar classes (under the International Union of Biochemistry), other examples of such combinations of oxidases and substrates are easily recognized by one skilled in the art.

Hydrogen peroxide or a source of hydrogen peroxide may be added at the beginning of or during the method of the invention, e.g. as one or more separate additions of hydrogen peroxide; or continuously as fed-batch addition. Typical amounts of hydrogen peroxide correspond to levels of from 0.001 mM to 25 mM, preferably to levels of from 0.005 mM to 5 mM, and particularly to levels of from 0.01 to 1 mM hydrogen peroxide. Hydrogen peroxide may also be used in an amount corresponding to levels of from 0.1 mM to 25 mM, preferably to levels of from 0.5 mM to 15 mM, more preferably to levels of from 1 mM to 10 mM, and most preferably to levels of from 2 mM to 8 mM hydrogen peroxide.

Surfactants

The method of the invention may include application of a surfactant (for example, as part of a detergent formulation or as a wetting agent). Surfactants suitable for being applied may be non-ionic (including semi-polar), anionic, cationic and/or zwitterionic; preferably the surfactant is anionic (such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap) or non-ionic (such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides")), or a mixture thereof.

When included in the method of the invention, the concentration of the surfactant will usually be from about 0.01% to about 10%, preferably about 0.05% to about 5%, and more preferably about 0.1% to about 1% by weight.

Aliphatic Hydrocarbons

The hydrocarbons, which are hydroxylated in the method of the invention, are aliphatic hydrocarbons having a chain of at least 3 carbons, and having a hydrogen attached to the carbon in position 2 or 3. Preferably, the aliphatic hydrocarbon is an alkane or an alkene; more preferably, the aliphatic hydrocarbon is an alkane, such as propane, butane, pentane, hexane, heptane, octane, nonane or decane, or isomers thereof.

The aliphatic hydrocarbons are linear or branched, but not cyclic, as site specific hydroxylation is not possible with cyclic hydrocarbons. Branched hydrocarbons correspond to isomers of linear hydrocarbons.

The aliphatic hydrocarbons are substituted or unsubstituted. Preferably, the aliphatic hydrocarbons are unsubstituted, such as non-activated hydrocarbons.

When the aliphatic hydrocarbons are substituted (functional groups attached), the preferred substituents are halogen, hydroxyl, carboxyl, amino, nitro, cyano, thiol, sulphonyl, formyl, acetyl, methoxy, ethoxy, phenyl, benzyl, xylyl, carbamoyl and sulfamoyl; more preferred substituents are chloro, hydroxyl, carboxyl and sulphonyl; and most preferred substituents are chloro and carboxyl.

The aliphatic hydrocarbons may be substituted by up to 10 substituents, up to 8 substituents, up to 6 substituents, up to 4 substituents, up to 2 substituents, or by up to one substituent.

In a preferred embodiment, the aliphatic hydrocarbon is a fatty acid (the substituent is a carboxyl group). Examples of fatty acids include, but are not limited to, butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), linoleic acid, linolenic acid, arachidonic acid, eicosapentaenoic acid, and docosahexaenoic acid.

In a second aspect, the aliphatic hydrocarbon is an acyl group of a lipid, such as a monoglyceride, diglyceride, triglyceride, phospholipid or sphingolipid; and the hydroxylation takes place in position 2 or position 3 of the terminal end of the acyl group. The acyl group must have at least one hydrogen attached to the carbon in position 2 or 3 of the terminal end. The acyl group may be saturated or unsaturated, and optionally functional groups (substituents) may be attached. Examples of acyl groups include, but are not limited to, the acyl forms of butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), linoleic acid, linolenic acid, arachidonic acid, eicosapentaenoic acid, and docosahexaenoic acid.

Methods and Uses

The present invention provides a method for site specific hydroxylation in position 2 or position 3 of an aliphatic hydrocarbon using a peroxygenase and hydrogen peroxide. The aliphatic hydrocarbon must include a chain of at least 3 carbons, and either (one or more) end of the aliphatic hydrocarbon may be used as the starting point to determine which carbon is in position 2 or 3. The aliphatic hydrocarbon must have at least one hydrogen attached to the carbon (which is hydroxylated) in position 2 or 3. In a preferred embodiment, the carbon in position 2 or 3, which is hydroxylated with the peroxygenase, is unsubstituted (before the hydroxylation is carried out).

Accordingly, in a first aspect, the present invention provides a method for hydroxylation in position 2 or 3 of either end (one or more ends) of a substituted or unsubstituted, linear or branched, aliphatic hydrocarbon having at least 3 carbons and having a hydrogen attached to the carbon in position 2 or 3, comprising contacting the aliphatic hydrocarbon with hydrogen peroxide and a polypeptide having peroxygenase activity; wherein the polypeptide comprises:

a) an amino acid sequence which has at least 50% identity to SEQ ID NO:1, SEQ ID NO:2, SEQ ID NO:3, SEQ ID NO:4, SEQ ID NO:5, SEQ ID NO:6, SEQ ID NO:7, or SEQ ID NO:8; and b) an amino acid sequence represented by one or more of the following motifs:

```
                                         (SEQ ID NO: 9)
Motif I:        [FL]XX[YF]S[AN]X[FHY]G[GN]GX[YF]N;

(SEQ ID NO: 10)
Motif II:       G[GN]GX[YF]NXX[VA]AX[EH][LF]R;

(SEQ ID NO: 11)
Motif III:      RXXRI[QE][DEQ]S[IM]ATN;

(SEQ ID NO: 12)
Motif IV:       S[IM]ATN[PG][EQN][FM][SDN][FL];

(SEQ ID NO: 13)
Motif V:        P[PDK][DG]F[HFW]R[AP];

(SEQ ID NO: 14)
Motif VI:       [TI]XXXLYPNP[TK][GV].
```

The method of the invention may be used for a variety of purposes, like bulk chemical synthesis (biocatalysis), increasing aqueous solubility of aliphatic hydrocarbons, bioremediation, and modification of the characteristics of food products.

The method of the invention may also be used for a number of industrial processes in which said hydroxylation reactions are beneficial. An example of such use is in the manufacture of pulp and paper products where alkanes and other relevant aliphatic hydrocarbons that are present in the wood (resin) can result in depositioning problems in the pulp and paper manufacturing process. These hydrophobic compounds are the precursors of the so-called pitch deposits within the pulp and paper manufacturing processes. Pitch deposition results in low quality pulp, and can cause the shutdown of pulp mill operations. Specific issues related to pulps with high extractives content include runnability problems, spots and holes in the paper, and sheet breaks. Treatment with peroxygenase can increase the solubility of said compounds and thereby mitigate problems.

Yet another use of the method of the invention is in i.e. oil or coal refineries where the peroxygenase catalyzed hydroxylation can be used to modify the solubility, viscosity and/or combustion characteristics of hydrocarbons. Specifically the treatment can lead to changes in the smoke point, the kindling point, the fire point and the boiling point of the hydrocarbons subjected to the treatment.

In the synthesis of bulk chemicals, agro chemicals (incl. pesticides), specialty chemicals and pharmaceuticals the method of the invention may obviously be relevant in terms of selectively introducing hydroxy groups in the substrates thereby affecting the solubility of the modified compound. Furthermore, the selective hydroxylation provides a site for further modification by methods known in the art of organic chemical synthesis and chemo-enzymatic synthesis.

Natural gas is extensively processed to remove higher alkanes. Hydroxylation of such higher alkanes may be used to improve water solubility, and thus facilitate removal of the higher alkanes by washing the natural gas stream. Removal may be performed at the well or during refining.

Hydroxylation of oil waste will significantly improve biodegradability and will be applicable both in connection with waste water treatment from refineries and bioremediation of contaminated ground or water In a second aspect, the present invention provides a method for hydroxylation in position 2 or 3 of the terminal end of an acyl group of a lipid, comprising contacting the lipid with hydrogen peroxide and a polypeptide having peroxygenase activity; wherein the polypeptide comprises:

a) an amino acid sequence which has at least 50% identity to SEQ ID NO:1, SEQ ID NO:2, SEQ ID NO:3, SEQ ID NO:4, SEQ ID NO:5, SEQ ID NO:6, SEQ ID NO:7, or SEQ ID NO:8; and b) an amino acid sequence represented by one or more of the following motifs:

```
                                         (SEQ ID NO: 9)
Motif I:        [FL]XX[YF]S[AN]X[FHY]G[GN]GX[YF]N (SEQ ID NO: 10)
Motif II:       G[GN]GX[YF]NXX[VA]AX[EH][LF]R (SEQ ID NO: 11)
Motif III:      RXXRI[QE][DEQ]S[IM]ATN (SEQ ID NO: 12)
Motif IV:       S[IM]ATN[PG][EQN][FM][SDN][FL]
```

Motif V:    P[PDK][DG]F[HFW]R[AP]         (SEQ ID NO: 13)

Motif VI:   [TI]XXXLYPNP[TK][GV].         (SEQ ID NO: 14)

Hydroxylation of the acyl group of a lipid generally improves the aqueous solubility of the lipid. Accordingly, the method of the invention may be used to remove or reduce oil or lipid containing stains, like chocolate, from laundry, by contacting the laundry with a peroxygenase and a source of hydrogen peroxide, and optionally a surfactant.

The methods of the invention may be carried out with an immobilized polypeptide having peroxygenase activity (peroxygenase).

The methods of the invention may be carried out in an aqueous solvent (reaction medium), various alcohols, ethers, other polar or non-polar solvents, or mixtures thereof. By studying the characteristics of the aliphatic hydrocarbon used in the methods of the invention, suitable examples of solvents are easily recognized by one skilled in the art. By raising or lowering the pressure at which the hydroxylation is carried out, the solvent (reaction medium) and the aliphatic hydrocarbon can be maintained in a liquid phase at the reaction temperature.

The methods according to the invention may be carried out at a temperature between 0 and 90° C., preferably between 5 and 80° C., more preferably between 10 and 70° C., even more preferably between 15 and 60° C., most preferably between 20 and 50° C., and in particular between 20 and 40° C.

The methods of the invention may employ a treatment time of from 10 seconds to (at least) 24 hours, preferably from 1 minute to (at least) 12 hours, more preferably from 5 minutes to (at least) 6 hours, most preferably from 5 minutes to (at least) 3 hours, and in particular from 5 minutes to (at least) 1 hour.

In another aspect, the methods of the invention may be used to reduce unpleasant odors from laundry by contacting the laundry with a peroxygenase and a source of hydrogen peroxide, and optionally a surfactant. The method of the invention results in reduction of the amount of butanoic acid (butyric acid) in the laundry. Butanoic acid is formed during washing of laundry when certain animal fats and plant oils are hydrolyzed, e.g. by detergent lipase, to yield free fatty acids, including butanoic acid. Butanoic acid has an extremely unpleasant odor. The peroxygenase hydroxylates the butanoic acid to 2-hydroxybutyric acid (alpha-hydroxybutyric acid) or 3-hydroxybutyric acid (beta-hydroxybutyric acid).

Unless otherwise specified, the nomenclature used is standard IUPAC nomenclature.

The present invention is further described by the following examples that should not be construed as limiting the scope of the invention.

EXAMPLES

The polypeptide having peroxygenase activity from *Agrocybe aegerita*, which is shown as SEQ ID NO:2, is referred to as AaeAPO in the following examples.

Example 1

Hydroxylation of n-Hexane

Enzymatic hydroxylation of hexane was performed in the pure substrate (n-hexane, >97%, Sigma Aldrich) containing 2 U ml$^{-1}$ (0.31 nmol) AaeAPO added as aqueous enzyme solution (10 µl). $H_2O_2$ (4 mM) was added by syringe pumps over 1 hour. The experiment was done in 200 µl scale (total volume) in 1 ml glass vials stirred with a magnetic stirrer. Products were analyzed by GC-MS (Varian) by direct injection of the reaction mixture. Controls were processed identically except that water (10 µl) was added instead of enzyme solution.

The gas chromatogram and mass spectra of the sample with active enzyme (AaeAPO) and n-hexane showed formation of high amounts of 2-hexanol, and 3-hexanol; the control without enzyme did not contain any of these peaks.

Example 2

Hydroxylation of n-Decane

Enzymatic conversion (in 200 µl total volume) was done in pure n-decane (>97%, Sigma Aldrich) supplemented with 2 U ml$^{-1}$ (0.31 nmol) AaeAPO. $H_2O_2$ (8 mM) was added by syringe pumps over 2 hours and the sample was stirred with a magnetic stirrer. Products were measured by GC-MS. Controls were processed identically except that water (10 µl) was added instead of enzyme.

The gas chromatogram and mass spectra of the sample with active enzyme (AaeAPO) and n-decane showed formation of high amounts of two n-alkanols, 3-decanol and 2-decanol; the control without enzyme did not contain these peaks.

Example 3

Enzymatic Hydroxylation of Lauric Acid

Enzymatic hydroxylation of lauric acid was performed using a total reaction mixture of 4 ml containing 50 mM potassium phosphate buffer, 40 v/v % acetonitrile, 1 mM lauric acid (>98% pure, Aldrich W261408 was dissolved in acetonitrile), 0.01 mg peroxygenase protein/ml (the peroxygenase shown as SEQ ID NO:4) and 2 mM ascorbic acid was added according to the table below.

The reaction was started by addition of hydrogen peroxide corresponding to a concentration of 0.5 mM in the reaction mixture. The reaction mixtures were incubated for 60 minutes at 35° C. using a heat block. A second addition of peroxide was added after 30 minutes incubation to a total concentration of 1 mM. The reactions were stopped by a heat treatment of 85° C. in a water bath for 5 minutes. Products were measured by GC-FID (Varian 3900) by injection at 100° C. in split mode with ratio of 10:1 (helium was used as carrier gas at a constant flow of 25 ml/min). A temperature gradient were applied heating to 200° C. at a rate of 10° C./min, then proceeding to 360° C. at a rate of 50° C./min. The results were recorded as peak area (see Table 1).

TABLE 1

| Treatment | Lauric acid (Area @3.2 min) | Product (Area @4.3 min) |
|---|---|---|
| Peroxygenase + $H_2O_2$ | No peak | No peak |
| Lauric acid + $H_2O_2$ + ascorbic acid | 16011 | 91 |
| Lauric acid + peroxygenase + $H_2O_2$ + ascorbic acid | 14406 | 395.5 |

A product peak appeared in the presence of the peroxygenase. The elution time of the product was slightly shifted compared to 12-Hydroxydodecanoic acid, which is an iso-form of 2-hydroxy lauric acid and 3-hydroxy lauric acid. Hence, the elution time was in accordance to the expected product hydroxylated in the 2 or 3 position.

Example 4

Enzymatic Hydroxylation of Palmitic Acid

Enzymatic hydroxylation of palmitic acid was performed using a total reaction mixture of 4 ml containing 50 mM potassium phosphate buffer, 40 v/v % acetonitrile, 1 mM palmitic acid (>99% pure, Sigma P0500) and 0.01 mg peroxygenase protein/ml (the peroxygenase shown as SEQ ID NO:4).

The reaction was started by addition of hydrogen peroxide corresponding to a concentration of 1 mM in the reaction mixture. The reaction mixtures were incubated for 1, 2, 3 and 10 minutes at 35° C. using a heat block. The reactions were stopped by a heat treatment of 85° C. in a water bath for 5 minutes. Products were measured by GC-FID (Varian 3900) by injection at 100° C. in split mode with ratio of 10:1 (helium was used as carrier gas at a constant flow of 25 ml/min). A temperature gradient were applied heating to 200° C. at a rate of 10° C./min, then proceeding to 360° C. at a rate of 50° C./min. The results were recorded as peak area (see Table 2).

TABLE 2

| Incubation time (min) | Palmitic acid (Area) | Product (Area) |
|---|---|---|
| 0 | 1799.5 | No peak |
| 1 | 1481.2 | 82.8 |
| 2 | 979.1 | 191.3 |

A product peak appeared already after 1 minutes of incubation, and increased after two minutes incubation. The elution profile was slightly shifted compared to 16-Hydroxy-hexadecanoic acid, which is an iso-form of 2-hydroxy palmitic and 3-hydroxy palmitic. Hence, the elution time was in accordance to the expected product hydroxylated in the 2 or 3 position.

The invention claimed is:

1. A method for hydroxylation in position 2 or 3 of either end of a substituted or unsubstituted, linear or branched, aliphatic hydrocarbon having at least 3 carbons and having a hydrogen attached to the carbon in position 2 or 3, comprising contacting the aliphatic hydrocarbon with hydrogen peroxide and a polypeptide having peroxygenase activity; wherein the polypeptide has at least 90% sequence identity to SEQ ID NO: 5.

2. The method of claim 1, wherein the carbon in position 2 or 3, which is hydroxylated, is unsubstituted until it is contacted with the peroxygenase.

3. The method of claim 1, wherein the amino acid sequence of the polypeptide comprises SEQ ID NO: 9.

4. The method of claim 1, wherein the amino acid sequence of the polypeptide comprises SEQ ID NO: 10.

5. The method of claim 1, wherein the amino acid sequence of the polypeptide comprises SEQ ID NO: 11.

6. The method of claim 1, wherein the amino acid sequence of the polypeptide comprises SEQ ID NO: 12.

7. The method of claim 1, wherein the amino acid sequence of the polypeptide comprises SEQ ID NO: 13.

8. The method of claim 1, wherein the amino acid sequence of the polypeptide comprises SEQ ID NO: 14.

9. The method of claim 1, wherein the polypeptide has at least 95% sequence identity to SEQ ID NO: 5.

10. The method of claim 1, wherein the polypeptide comprises or consists of the amino acid sequence of SEQ ID NO: 5.

11. The method of claim 1, wherein the substituents of the aliphatic hydrocarbon are selected from the group consisting of halogen, hydroxyl, carboxyl, amino, nitro, cyano, thiol, sulphonyl, formyl, acetyl, methoxy, ethoxy, phenyl, benzyl, xylyl, carbamoyl and sulfamoyl.

12. The method of claim 1, wherein the substituents are selected from the group consisting of chloro, hydroxyl, carboxyl and sulphonyl; in particular chloro and carboxyl.

13. The method of claim 1, wherein the aliphatic hydrocarbon is unsubstituted.

14. The method of claim 1, wherein the aliphatic hydrocarbon is linear.

15. The method of claim 1, wherein the aliphatic hydrocarbon is an alkane.

16. The method of claim 15, wherein the alkane is propane, butane, pentane, hexane, heptane, octane, nonane or decane, or isomers thereof.

17. The method of claim 1, wherein the aliphatic hydrocarbon is part of a fatty acid.

18. A method for hydroxylation in position 2 or 3 of the terminal end of an acyl group of a lipid, comprising contacting the lipid with hydrogen peroxide and a polypeptide having peroxygenase activity; wherein the polypeptide has at least 90% sequence identity to SEQ ID NO: 5.

19. The method of claim 18, wherein the polypeptide has at least 95% identity to SEQ ID NO: 5.

* * * * *

SEQUENCE LISTING

```
<160> NUMBER OF SEQ ID NOS: 14

<210> SEQ ID NO 1
<211> LENGTH: 330
<212> TYPE: PRT
<213> ORGANISM: Agrocybe aegerita
<220> FEATURE:
<221> NAME/KEY: mat_peptide
<222> LOCATION: (1)..(330)

<400> SEQUENCE: 1
```

Glu Pro Thr Gln Pro Pro Gly Pro Pro Glu Asp Thr Ser Ala Lys Leu
1               5                   10                  15

Val Asn Asp Lys Asp His Pro Trp Lys Pro Leu Arg Pro Gly Asp Ile
                20                  25                  30

Arg Gly Pro Cys Pro Gly Leu Asn Thr Leu Ala Ser His Gly Tyr Leu
            35                  40                  45

Pro Arg Asn Gly Val Ala Thr Pro Ala Gln Ile Ile Asn Ala Val Gln
        50                  55                  60

Glu Gly Phe Asn Met Asp Asn Ser Val Ala Leu Phe Ala Thr Tyr Glu
65                  70                  75                  80

Ala His Leu Met Val Gly Asn Leu Leu Thr Asp Leu Leu Ser Ile Gly
                85                  90                  95

Arg Lys Thr Pro Leu Thr Gly Pro Asp Leu Pro Pro Pro Ala Asn Ile
            100                 105                 110

Gly Gly Leu Ser Glu His Gly Leu Phe Glu Gly Asp Ala Ser Met Thr
        115                 120                 125

Arg Gly Asp Ala Phe Phe Gly Asn Asn Asp Glu Phe Asn Glu Glu Leu
    130                 135                 140

Phe Gln Gln Phe Ile Asp Tyr Ser Asn Arg Phe Gly Gly Gly Tyr Tyr
145                 150                 155                 160

Asn Leu Thr Val Ala Val Glu Leu Arg Phe Lys Arg Ile Gln Asp Ser
                165                 170                 175

Ile Ala Thr Asn Pro Glu Phe Asn Phe Val Ser Pro Arg Phe Phe Ala
            180                 185                 190

Ala Tyr Gly Glu Ser Val Ala Pro Asn Asn Phe Phe Val Asp Gly Arg
        195                 200                 205

```
Lys Asp Asp Gly His Leu Asp Met Asp Ala Ala Arg Gly Phe Phe Gln
            210                 215                 220

Phe Gly Arg Met Pro Asp Gly Phe Phe Arg Pro Asn Gly Thr Lys Gly
225                 230                 235                 240

Asn Ala Gly Leu Asp Asp Val Val Arg Ala His Pro Val Gln Pro Gly
                245                 250                 255

Arg Asn Leu Gly Arg Val Asn Ser Tyr Thr His Asp Pro Thr Ser Ala
                260                 265                 270

Asp Phe Thr Thr Pro Cys Leu Leu Tyr Glu Asn Phe Ala Asn Lys Thr
                275                 280                 285

Val Thr Ala Leu Tyr Pro Asn Pro Lys Gly Gln Leu Arg Arg Ala Ile
            290                 295                 300

Lys Ala Asn Leu His Phe Leu Phe Leu Ala Ile Asn Arg Thr Val Gly
305                 310                 315                 320

Cys Ala Glu Val Phe Pro Tyr Gly Arg Asp
                325                 330

<210> SEQ ID NO 2
<211> LENGTH: 328
<212> TYPE: PRT
<213> ORGANISM: Agrocybe aegerita
<220> FEATURE:
<221> NAME/KEY: mat_peptide
<222> LOCATION: (1)..(328)

<400> SEQUENCE: 2

Glu Pro Gly Leu Pro Pro Gly Pro Leu Glu Asn Ser Ser Ala Lys Leu
1               5                   10                  15

Val Asn Asp Glu Ala His Pro Trp Lys Pro Leu Arg Pro Gly Asp Ile
            20                  25                  30

Arg Gly Pro Cys Pro Gly Leu Asn Thr Leu Ala Ser His Gly Tyr Leu
            35                  40                  45

Pro Arg Asn Gly Val Ala Thr Pro Val Gln Ile Ile Asn Ala Val Gln
        50                  55                  60

Glu Gly Leu Asn Phe Asp Asn Gln Ala Ala Val Phe Ala Thr Tyr Ala
65                  70                  75                  80

Ala His Leu Val Asp Gly Asn Leu Ile Thr Asp Leu Leu Ser Ile Gly
                85                  90                  95

Arg Lys Thr Arg Leu Thr Gly Pro Asp Pro Pro Pro Ala Ser Val
            100                 105                 110

Gly Gly Leu Asn Glu His Gly Thr Phe Glu Gly Asp Ala Ser Met Thr
            115                 120                 125

Arg Gly Asp Ala Phe Phe Gly Asn Asn His Asp Phe Asn Glu Thr Leu
130                 135                 140

Phe Glu Gln Leu Val Asp Tyr Ser Asn Arg Phe Gly Gly Lys Tyr
145                 150                 155                 160

Asn Leu Thr Val Ala Gly Glu Leu Arg Phe Lys Arg Ile Gln Asp Ser
                165                 170                 175

Ile Ala Thr Asn Pro Asn Phe Ser Phe Val Asp Phe Arg Phe Phe Thr
                180                 185                 190

Ala Tyr Gly Glu Thr Thr Phe Pro Ala Asn Leu Phe Val Asp Gly Arg
            195                 200                 205

Arg Asp Asp Gly Gln Leu Asp Met Asp Ala Ala Arg Ser Phe Phe Gln
210                 215                 220

Phe Ser Arg Met Pro Asp Asp Phe Phe Arg Ala Pro Ser Pro Arg Ser
```

```
                225                 230                 235                 240
Gly Thr Gly Val Glu Val Ile Gln Ala His Pro Met Gln Pro Gly
                245                 250                 255

Arg Asn Val Gly Lys Ile Asn Ser Tyr Thr Val Asp Pro Thr Ser Ser
            260                 265                 270

Asp Phe Ser Thr Pro Cys Leu Met Tyr Glu Lys Phe Val Asn Ile Thr
            275                 280                 285

Val Lys Ser Leu Tyr Pro Asn Pro Thr Val His Val Arg Lys Ala Leu
            290                 295                 300

Asn Thr Asn Leu Asp Phe Phe Gln Gly Val Ala Ala Gly Cys Thr
305                 310                 315                 320

Gln Val Phe Pro Tyr Gly Arg Asp
                325

<210> SEQ ID NO 3
<211> LENGTH: 377
<212> TYPE: PRT
<213> ORGANISM: Laccaria bicolor

<400> SEQUENCE: 3

Met Ala Arg Leu Thr Phe Leu Ala Ala Ile Ala Leu Ala Leu Ser Ser
1               5                   10                  15

Thr Thr Val Leu Ala Phe Pro Ser Tyr Gly Ser Leu Ala Gly Leu Ser
            20                  25                  30

Glu Ala Glu Leu Asp Arg Ile Ile Pro Leu Leu Glu Ala Arg Asn Ala
        35                  40                  45

Gly Pro Pro Gly Pro Leu Lys Asn Thr Ser Thr Lys Leu Val Asn
    50                  55                  60

Asp Lys Asn His Pro Trp Lys Pro Leu Gly Tyr Gly Asp Ile Arg Gly
65                  70                  75                  80

Pro Cys Pro Gly Leu Asn Thr Leu Ala Ser His Gly Trp Leu Pro Arg
                85                  90                  95

Asn Gly Ile Ala Thr Pro Ala Gln Ile Val Asn Ala Val Gln Glu Gly
            100                 105                 110

Phe Asn Met Gly Asn Asp Leu Ala Val Phe Val Thr Tyr Ala Ala His
        115                 120                 125

Leu Val Asp Gly Asn Gln Val Thr Asp Leu Leu Ser Ile Gly Gly Lys
    130                 135                 140

Thr Pro Gln Thr Gly Pro Asp Pro Ala Pro Ala Ile Val Gly Gly
145                 150                 155                 160

Leu Asn Thr His Ala Val Phe Glu Gly Asp Ala Ser Met Thr Arg Gly
                165                 170                 175

Asp Ala Phe Phe Gly Asp Asn His Ser Phe Asn Glu Thr Gln Phe Asp
            180                 185                 190

Glu Phe Ser Ala Phe Ser Asn Lys Phe Gly Gly Gly Tyr Tyr Asn Leu
        195                 200                 205

Ser Val Ala Ala Glu Phe Arg Trp Gln Arg Ile Gln Glu Ser Ile Ala
    210                 215                 220

Thr Asn Pro Asn Phe Ser Leu Ile Ser Pro Arg Tyr Phe Thr Ala Tyr
225                 230                 235                 240

Ala Glu Ser Val Phe Pro Leu Val Phe Val Asp Gly Arg Val Ser
                245                 250                 255

Asp Gly Arg Leu Ser Leu Pro Asn Ala Arg Gly Phe Phe Gln Asn Ser
            260                 265                 270
```

```
Gln Met Pro Lys Asp Phe Phe Arg Pro Asn Gln Ser Ile Gly Leu Asn
            275                 280                 285

Glu Ile Gly Asp Gly Ile Ser Ala Ile Ala Ser Ala His Pro Ile Ala
        290                 295                 300

Pro Gly Lys Asn Glu Gly Val Gly Asn Tyr Val Leu Asp Pro Thr Ser
305                 310                 315                 320

Ala Asp Phe Asp His Phe Cys Leu Leu Tyr Ile Asn Phe Val Asn Gln
                325                 330                 335

Thr Val Lys Ser Leu Tyr Pro Asn Pro Lys Gly Val Leu Leu Asp Ala
            340                 345                 350

Leu Lys Arg Asn Leu Asn Asn Phe Tyr Gly Pro Leu Asn Gly Ser Asp
        355                 360                 365

Cys Glu Gln Ile Phe Pro Tyr Gly Lys
370                 375

<210> SEQ ID NO 4
<211> LENGTH: 344
<212> TYPE: PRT
<213> ORGANISM: Coprinopsis cinerea
<220> FEATURE:
<221> NAME/KEY: mat_peptide
<222> LOCATION: (1)..(344)

<400> SEQUENCE: 4

Thr Ser Lys Leu Pro Ile Val Phe Pro Pro Pro Pro Glu Pro Ile
1               5                   10                  15

Lys Asp Pro Trp Leu Lys Leu Val Asn Asp Arg Ala His Pro Trp Arg
            20                  25                  30

Pro Leu Arg Arg Gly Asp Val Arg Gly Pro Cys Pro Gly Leu Asn Thr
        35                  40                  45

Leu Ala Ser His Gly Tyr Leu Pro Arg Asp Gly Val Ala Thr Pro Ala
    50                  55                  60

Gln Ile Ile Thr Ala Val Gln Glu Gly Phe Asn Met Glu Tyr Gly Ile
65                  70                  75                  80

Ala Thr Phe Val Thr Tyr Ala Ala His Leu Val Asp Gly Asn Pro Leu
                85                  90                  95

Thr Asn Leu Ile Ser Ile Gly Gly Lys Thr Arg Lys Thr Gly Pro Asp
            100                 105                 110

Pro Pro Pro Pro Ala Ile Val Gly Gly Leu Asn Thr His Ala Val Phe
        115                 120                 125

Glu Gly Asp Ala Ser Met Thr Arg Gly Asp Phe His Leu Gly Asp Asn
    130                 135                 140

Phe Asn Phe Asn Gln Thr Leu Trp Glu Gln Phe Lys Asp Tyr Ser Asn
145                 150                 155                 160

Arg Tyr Gly Gly Gly Arg Tyr Asn Leu Thr Ala Ala Ala Glu Leu Arg
                165                 170                 175

Trp Ala Arg Ile Gln Gln Ser Met Ala Thr Asn Gly Gln Phe Asp Phe
            180                 185                 190

Thr Ser Pro Arg Tyr Phe Thr Ala Tyr Ala Glu Ser Val Phe Pro Ile
        195                 200                 205

Asn Phe Phe Thr Asp Gly Arg Leu Phe Thr Ser Asn Thr Thr Ala Pro
    210                 215                 220

Gly Pro Asp Met Asp Ser Ala Leu Ser Phe Phe Arg Asp His Arg Tyr
225                 230                 235                 240

Pro Lys Asp Phe His Arg Ala Pro Val Pro Ser Gly Ala Arg Gly Leu
                245                 250                 255
```

```
Asp Val Ala Ala Ala Tyr Pro Ile Gln Pro Gly Tyr Asn Ala Asp
            260                 265                 270

Gly Lys Val Asn Asn Tyr Val Leu Asp Pro Thr Ser Ala Asp Phe Thr
        275                 280                 285

Lys Phe Cys Leu Leu Tyr Glu Asn Phe Val Leu Lys Thr Val Lys Gly
    290                 295                 300

Leu Tyr Pro Asn Pro Lys Gly Phe Leu Arg Lys Ala Leu Glu Thr Asn
305                 310                 315                 320

Leu Glu Tyr Phe Tyr Gln Ser Phe Pro Gly Ser Gly Cys Pro Gln
                325                 330                 335

Val Phe Pro Trp Gly Lys Ser Asp
            340
```

<210> SEQ ID NO 5
<211> LENGTH: 351
<212> TYPE: PRT
<213> ORGANISM: Coprinopsis cinerea

<400> SEQUENCE: 5

```
Met Val Ser Cys Lys Leu Pro Leu Leu Thr Leu Ala Ile Ala
1               5                   10                  15

Leu Ala Asn Val Asn Ala Phe Pro Ala Tyr Gln Ser Leu Gly Gly Leu
            20                  25                  30

Ser Lys Arg Gln Leu Glu Thr Ile Ile Pro Gly Leu Pro Val Val Asn
        35                  40                  45

Pro Gly Pro Pro Gly Pro Leu Ala Asp Ser Thr Leu Lys Leu Val
    50                  55                  60

Asn Asp Ala Ala His Pro Tyr Gln Ala Pro Arg Pro His Leu Asp His
65                  70                  75                  80

Arg Gly Pro Cys Pro Gly Leu Asn Thr Leu Ala Asn His Gly Tyr Leu
                85                  90                  95

Pro Arg Ser Gly Ile Ala Thr Pro Ala Gln Ile Val Gln Ala Val Met
            100                 105                 110

Glu Gly Phe Asn Met Glu Asn Thr Phe Ala Lys Phe Val Thr Tyr Ala
            115                 120                 125

Ala Phe Leu Val Asp Gly Asn Pro Ile Thr Asn Leu Met Ser Ile Gly
        130                 135                 140

Gly Lys Thr Trp Arg Thr Gly Ile Ile Glu Pro Pro Pro Ala Ile
145                 150                 155                 160

Val Gly Gly Leu Asn Thr His Ala Val Phe Glu Gly Asp Thr Ser Met
                165                 170                 175

Thr Arg Gly Asp Phe His Phe Gly Asp Asn His Ser Phe Asn Gln Thr
            180                 185                 190

Leu Phe Asp Gln Phe Val Glu Tyr Ser Asn Ile His Gly Gly Gly Phe
        195                 200                 205

Tyr Asn Leu Thr Ala Ala Thr Glu Leu Arg Tyr Gln Arg Ile Gln Gln
    210                 215                 220

Ser Ile Ala Thr Asn Pro Glu Met Ser Phe Val Ser Pro Arg Trp Phe
225                 230                 235                 240

Thr Ala Ile Leu Leu Gln Asp Glu Lys Phe Pro Asp Asp Phe His Arg
                245                 250                 255

Ala Pro Gly Pro Phe Ser Phe Glu Gly Leu Gly Tyr Leu Val Thr Arg
            260                 265                 270

Arg Pro Met Pro Pro Gly Arg Asn Val Gly Gly Val Asp Asn Tyr Val
```

```
              275                 280                 285
Pro Asp Pro Asn Ser Ala Asp Phe Asn Ser Phe Cys Lys Met Tyr Glu
    290                 295                 300

Asp Phe Val Asn Asp Ile Val Val Ala Leu Tyr Pro Asn Pro Thr Gly
305                 310                 315                 320

Leu Leu Arg Arg Asn Leu Ile Lys Asn Leu Glu Tyr Phe Trp Thr Gly
                    325                 330                 335

Met Phe Asp Pro Ala Cys Thr Glu Val Lys Pro Tyr Gly Thr Leu
                340                 345                 350

<210> SEQ ID NO 6
<211> LENGTH: 386
<212> TYPE: PRT
<213> ORGANISM: Coprinopsis cinerea

<400> SEQUENCE: 6

Met Asn Gly Leu Phe Ala Thr Val Lys Leu Ala Leu Val Thr Leu Leu
1               5                   10                  15

Ala Ser Gln Ser Gln Phe Ala Asn Ala Phe Pro Ala Trp Gln Ser Leu
                20                  25                  30

Gly Gly Leu Ser Glu Arg Gln Leu Asp Glu Val Met Pro Met Leu Lys
            35                  40                  45

His Arg Val Pro Pro Pro Pro Gly Pro Pro Ala Phe Thr Gly Ala
    50                  55                  60

Lys Leu Val Asn Asp Lys Ala His Pro Phe Lys Pro Leu Lys Lys Gly
65                  70                  75                  80

Asp Val Arg Gly Pro Cys Pro Gly Leu Asn Thr Leu Ala Ser His Gly
                85                  90                  95

Tyr Leu Pro Arg Asn Gly Val Ala Ser Pro Ser Gln Ile Ile Asp Ala
            100                 105                 110

Val Gln Glu Gly Phe Asn Met Glu Asn Glu Leu Ala Arg Phe Thr Thr
        115                 120                 125

Tyr Val Ala His Leu Val Asp Gly Asn Leu Val Thr Asp Leu Leu Ser
    130                 135                 140

Ile Gly Glu Lys Thr Arg Lys Thr Gly Pro Asp Pro Pro Pro Ala
145                 150                 155                 160

Ile Val Gly Gly Leu Asn Asn His Gly Thr Phe Glu Gly Asp Ala Ser
                165                 170                 175

Leu Thr Arg Gly Asp Ala Phe Phe Gly Asp Asn His Asn Phe Asn Gln
            180                 185                 190

Glu Leu Phe Asp Gln Phe Lys Asn Phe Ser Ala Val Tyr Gly Asn Gly
        195                 200                 205

Phe Phe Asn Met Thr Val Ala Gly Glu Leu Arg Phe His Arg Ile Gln
    210                 215                 220

Gln Ser Ile Ala Thr Asn Pro Glu Phe Ser Leu Val Gly Leu Arg His
225                 230                 235                 240

Leu Thr Ala Tyr Ala Glu Ala Ser Phe Pro Ser Leu Phe Phe Val Asp
                245                 250                 255

Gly Arg Lys Thr Gly Ala Glu Ala Gly Gln Leu Asp Met Ala Thr Ala
            260                 265                 270

Glu Ser Phe Phe Arg Asp Met Met Tyr Pro Pro Asp Phe Phe Arg Pro
        275                 280                 285

Ala Ala Pro Val Ala Gly Asp Gly Ala Ile Phe Leu Ala His Pro
    290                 295                 300
```

```
Phe Gln Pro Gly Arg Asn Val Gly Gly Val Asn Asn Phe Thr Val Asp
305                 310                 315                 320

Asp Ser Leu Gly Ser Leu Leu Asp Phe Cys Gly Phe Tyr Glu Asn Phe
            325                 330                 335

Val Asn Lys Thr Leu Lys Ala Leu Tyr Pro Asn Pro Lys Gly Val Leu
        340                 345                 350

Arg Arg Asn Leu Asn Ile Asn Leu Gln Phe Phe Glu Ser Leu Pro
    355                 360                 365

Lys Asp Glu Ser Gly Thr Pro Val Cys Thr Gln Val Phe Pro Tyr Gly
    370                 375                 380

Arg Asn
385

<210> SEQ ID NO 7
<211> LENGTH: 341
<212> TYPE: PRT
<213> ORGANISM: Coprinopsis cinerea

<400> SEQUENCE: 7

Met Leu Lys Pro Arg Val Pro Pro Pro Gly Pro Leu Ala Phe
1               5                   10                  15

Asn Gly Thr Lys Leu Val Asn Asp Glu Asp His Pro Phe Met Pro Pro
            20                  25                  30

Arg Lys Gly Asp Ala Arg Gly Pro Cys Pro Gly Leu Asn Thr Leu Ala
        35                  40                  45

Ser His Gly Tyr Leu Pro Arg Asn Gly Ile Ala Thr Pro Ala Gln Ile
    50                  55                  60

Ile Asn Ala Val Gln Glu Gly Phe Asn Met Glu Asn Glu Ile Ala Arg
65                  70                  75                  80

Phe Thr Thr Tyr Thr Ala His Leu Met Asp Gly Asn Leu Val Thr Asp
                85                  90                  95

Leu Leu Ser Ile Gly Pro Lys Thr Pro Lys Thr Gly Pro Asp Pro Pro
            100                 105                 110

Pro Pro Ala Ile Val Gly Gly Leu Asn Asn His Gly Thr Phe Glu Gly
        115                 120                 125

Asp Ala Ser Leu Ser Arg Ala Asp Ala Phe Phe Gly Asp Asn His Ser
    130                 135                 140

Phe Asp Gln Glu Leu Phe Asp Gln Phe Arg Asn Phe Ser Ala Ile Tyr
145                 150                 155                 160

Gly Asn Gly Phe Phe Asn Met Thr Val Ala Ala Glu Leu Arg Phe His
                165                 170                 175

Arg Ile Gln Gln Ser Ile Ala Thr Asn Pro Glu Phe Ser Phe Ala Gly
            180                 185                 190

Leu Arg His Ile Thr Ala Tyr Ala Glu Ala Ser Phe Pro Pro Ile Phe
        195                 200                 205

Phe Val Asp Gly Arg Lys Thr Gly Ala Glu Ala Gly Gln Leu Asp Met
    210                 215                 220

Ala Ala Ala Glu Ser Phe Phe Lys His Met Met Tyr Pro Pro Asp Phe
225                 230                 235                 240

His Arg Pro Ala Glu Pro Val Asn Ser Asp Ala Gln Ala Val Phe Glu
                245                 250                 255

Val His Pro Phe Gln Pro Gly Arg Asn Val Gly Gly Val Asn Asn Tyr
            260                 265                 270

Thr Val Asp Glu Ser Leu Gly Gly Leu Leu Asp Phe Cys Gly Phe Tyr
        275                 280                 285
```

```
Glu Asn Phe Val Asn Lys Thr Ile Lys Gly Leu Tyr Pro Asn Pro Thr
    290                 295                 300

Gly Val Leu Lys Arg Asn Leu Asn Ile Asn Leu Asp Phe Leu Phe Glu
305                 310                 315                 320

Ala Leu Pro Lys Ala Gly Asp Gly Ser Gln Pro Cys Thr Gln Val Phe
                325                 330                 335

Pro Tyr Gly His Asp
            340

<210> SEQ ID NO 8
<211> LENGTH: 325
<212> TYPE: PRT
<213> ORGANISM: Coprinus radians

<400> SEQUENCE: 8

Pro Pro Pro Glu Tyr Val Gly Pro Lys Leu Val Asn Asp Ala Asp His
1               5                   10                  15

Pro Trp Glu Pro Leu Arg Pro Gly Asp Ile Arg Gly Pro Cys Pro Gly
            20                  25                  30

Leu Asn Thr Leu Ala Ser His Gly Tyr Leu Pro Arg Asn Gly Val Ala
        35                  40                  45

Thr Pro Ala Gln Ile Ile Asn Ala Ile Val Glu Gly Phe Asn Phe Asn
    50                  55                  60

Tyr Glu Gly Ala Val Phe Val Thr Tyr Phe Ala His Ile Val Asp Gly
65                  70                  75                  80

Asn Leu Val Thr Asp Leu Leu Ser Ile Gly Gly Lys Thr Asn Leu Thr
                85                  90                  95

Gly Glu Asp Thr Gly Ala Pro Ala Ile Ile Gly Gly Leu Asn Thr His
            100                 105                 110

Ser Val Phe Glu Gly Asp Ala Ser Met Thr Arg Asp Asp Phe His Phe
        115                 120                 125

Gly Asp Asn His Ser Phe Asn Gln Thr Leu Phe Asp Gln Phe Val Glu
    130                 135                 140

Tyr Ser Asn Thr Tyr Gly Gly Gly Phe Tyr Asn Gln Glu Val Ala Gly
145                 150                 155                 160

His Leu Arg Arg Arg Arg Ile Glu Gln Ser Ile Ala Thr Asn Pro Glu
                165                 170                 175

Phe Asp Phe Thr Ser Pro Arg Phe Phe Thr Ala Phe Ala Glu Ser Ser
            180                 185                 190

Phe Pro Tyr Ser Phe Phe Val Asp Gly Arg Ile Thr Glu Arg Pro Gly
        195                 200                 205

Gly Leu Ser Met Glu Asn Ala Thr Leu Phe Phe Arg Asp His Lys Met
    210                 215                 220

Pro Asp Asp Phe Trp Arg Ala Pro Glu Pro Thr Gly Gly Leu Asn Val
225                 230                 235                 240

Leu Asp Ile Tyr Arg Ala Ser Gly Ser Pro Pro Ala Gly Arg Asn Val
                245                 250                 255

Asn Gly Thr Asn Thr Phe Thr Pro Asp Pro Asn Ser Ala Asp Phe Asp
            260                 265                 270

Asn Pro Cys Glu Leu Tyr Tyr Asp Tyr Val Asn Arg Ile Val Lys Ser
        275                 280                 285

Leu Tyr Pro Asn Pro Thr Gly Ile Leu Arg Asp Asn Leu Asn Ile Ala
    290                 295                 300

Leu Gly His Val Phe Asp Ser Met Asp Phe Gly Asp Cys Glu Gln Leu
```

```
305                 310                 315                 320

Phe Pro Tyr Gly Arg
            325

<210> SEQ ID NO 9
<211> LENGTH: 14
<212> TYPE: PRT
<213> ORGANISM: Artificial sequence
<220> FEATURE:
<223> OTHER INFORMATION: Peroxygenase motif I
<220> FEATURE:
<221> NAME/KEY: VARIANT
<222> LOCATION: (1)..(1)
<223> OTHER INFORMATION: The amino acid may be Phe or Leu.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: The amino acid may be Tyr or Phe.
<220> FEATURE:
<221> NAME/KEY: VARIANT
<222> LOCATION: (6)..(6)
<223> OTHER INFORMATION: The amino acid may be Ala or Asn.
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: VARIANT
<222> LOCATION: (8)..(8)
<223> OTHER INFORMATION: The amino acid may be Phe, His or Tyr.
<220> FEATURE:
<221> NAME/KEY: VARIANT
<222> LOCATION: (10)..(10)
<223> OTHER INFORMATION: The amino acid may be Gly or Asn.
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: The amino acid may be Tyr or Phe.

<400> SEQUENCE: 9

Xaa Xaa Xaa Xaa Ser Xaa Xaa Xaa Gly Xaa Gly Xaa Xaa Asn
1               5                   10

<210> SEQ ID NO 10
<211> LENGTH: 14
<212> TYPE: PRT
<213> ORGANISM: Artificial sequence
<220> FEATURE:
<223> OTHER INFORMATION: Peroxygenase motif II
<220> FEATURE:
<221> NAME/KEY: VARIANT
<222> LOCATION: (2)..(2)
<223> OTHER INFORMATION: The amino acid may be Gly or Asn.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: VARIANT
<222> LOCATION: (5)..(5)
<223> OTHER INFORMATION: The amino acid may be Tyr or Phe.
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: VARIANT
```

```
<222> LOCATION: (9)..(9)
<223> OTHER INFORMATION: The amino acid may be Val or Ala.
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: The amino acid may be Glu or His.
<220> FEATURE:
<221> NAME/KEY: VARIANT
<222> LOCATION: (13)..(13)
<223> OTHER INFORMATION: The amino acid may be Leu or Phe.

<400> SEQUENCE: 10

Gly Xaa Gly Xaa Xaa Asn Xaa Xaa Xaa Ala Xaa Xaa Xaa Arg
1               5                   10

<210> SEQ ID NO 11
<211> LENGTH: 12
<212> TYPE: PRT
<213> ORGANISM: Artificial sequence
<220> FEATURE:
<223> OTHER INFORMATION: Peroxygenase motif III
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: The amino acid may be Gln or Glu.
<220> FEATURE:
<221> NAME/KEY: VARIANT
<222> LOCATION: (7)..(7)
<223> OTHER INFORMATION: The amino acid may be Asp, Glu or Gln.
<220> FEATURE:
<221> NAME/KEY: VARIANT
<222> LOCATION: (9)..(9)
<223> OTHER INFORMATION: The amino acid may be Ile or Met.

<400> SEQUENCE: 11

Arg Xaa Xaa Arg Ile Xaa Xaa Ser Xaa Ala Thr Asn
1               5                   10

<210> SEQ ID NO 12
<211> LENGTH: 10
<212> TYPE: PRT
<213> ORGANISM: Artificial sequence
<220> FEATURE:
<223> OTHER INFORMATION: Peroxygenase motif IV
<220> FEATURE:
<221> NAME/KEY: VARIANT
<222> LOCATION: (2)..(2)
<223> OTHER INFORMATION: The amino acid may be Ile or Met.
<220> FEATURE:
<221> NAME/KEY: VARIANT
<222> LOCATION: (6)..(6)
<223> OTHER INFORMATION: The amino acid may be Pro or Gly.
<220> FEATURE:
<221> NAME/KEY: VARIANT
<222> LOCATION: (7)..(7)
<223> OTHER INFORMATION: The amino acid may be Glu, Gln or Asn.
<220> FEATURE:
<221> NAME/KEY: VARIANT
<222> LOCATION: (8)..(8)
<223> OTHER INFORMATION: The amino acid may be Phe or Met.
<220> FEATURE:
<221> NAME/KEY: VARIANT
<222> LOCATION: (9)..(9)
<223> OTHER INFORMATION: The amino acid may be Ser, Asp or Asn.
<220> FEATURE:
<221> NAME/KEY: VARIANT
<222> LOCATION: (10)..(10)
```

-continued

```
<223> OTHER INFORMATION: The amino acid may be Phe or Leu.

<400> SEQUENCE: 12

Ser Xaa Ala Thr Asn Xaa Xaa Xaa Xaa Xaa
1               5                   10

<210> SEQ ID NO 13
<211> LENGTH: 7
<212> TYPE: PRT
<213> ORGANISM: Artificial sequence
<220> FEATURE:
<223> OTHER INFORMATION: Peroxygenase motif V
<220> FEATURE:
<221> NAME/KEY: VARIANT
<222> LOCATION: (2)..(2)
<223> OTHER INFORMATION: The amino acid may be Pro, Asp or Lys.
<220> FEATURE:
<221> NAME/KEY: VARIANT
<222> LOCATION: (3)..(3)
<223> OTHER INFORMATION: The amino acid may be Asp or Gly.
<220> FEATURE:
<221> NAME/KEY: VARIANT
<222> LOCATION: (5)..(5)
<223> OTHER INFORMATION: The amino acid may be His, Phe or Trp.
<220> FEATURE:
<221> NAME/KEY: VARIANT
<222> LOCATION: (7)..(7)
<223> OTHER INFORMATION: The amino acid may be Ala or Pro.

<400> SEQUENCE: 13

Pro Xaa Xaa Phe Xaa Arg Xaa
1               5

<210> SEQ ID NO 14
<211> LENGTH: 11
<212> TYPE: PRT
<213> ORGANISM: Artificial sequence
<220> FEATURE:
<223> OTHER INFORMATION: Peroxygenase motif VI
<220> FEATURE:
<221> NAME/KEY: VARIANT
<222> LOCATION: (1)..(1)
<223> OTHER INFORMATION: The amino acid may be Thr or Ile.
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: The amino acid may be Thr or Lys.
<220> FEATURE:
<221> NAME/KEY: VARIANT
<222> LOCATION: (11)..(11)
<223> OTHER INFORMATION: The amino acid may be Gly or Val.

<400> SEQUENCE: 14

Xaa Xaa Xaa Xaa Leu Tyr Pro Asn Pro Xaa Xaa
1               5                   10
```